United States Patent
Levitsky et al.

(12)
(10) Patent No.: US 6,686,206 B2
(45) Date of Patent: Feb. 3, 2004

(54) METHOD OF SIGNAL AMPLIFICATION IN MULTI-CHROMOPHORE LUMINESCENCE SENSORS

(75) Inventors: Igor A. Levitsky, Fall River, MA (US); Sergei G. Krivoshlykov, Shrewsbury, MA (US)

(73) Assignee: ALTAIR Center, LLC, Shrewsburg, MA (US)

( * ) Notice: Subject to any disclaimer, the term of this patent is extended or adjusted under 35 U.S.C. 154(b) by 385 days.

(21) Appl. No.: 09/826,254

(22) Filed: Apr. 4, 2001

(65) Prior Publication Data

US 2003/0032197 A1 Feb. 13, 2003

(51) Int. Cl.$^7$ .............................................. G01N 21/64
(52) U.S. Cl. ...................................... 436/104; 436/172
(58) Field of Search ................................ 436/104, 164, 436/172; 250/458.1, 459.1; 422/82.07, 82.08, 82.11

(56) References Cited

U.S. PATENT DOCUMENTS

| | | | | |
|---|---|---|---|---|
| 4,682,895 A | * | 7/1987 | Costello | 356/402 |
| 5,512,490 A | * | 4/1996 | Walt et al. | 436/171 |
| 6,015,869 A | * | 1/2000 | Grate et al. | 528/15 |
| 6,103,535 A | * | 8/2000 | Pilevar et al. | 436/518 |
| 6,300,638 B1 | * | 10/2001 | Groger et al. | 250/458.1 |

FOREIGN PATENT DOCUMENTS

WO        WO 99/01737         * 1/1999

* cited by examiner

*Primary Examiner*—Jeffrey Snay

(57) ABSTRACT

A fluorescence-based method for highly sensitive and selective detection of analyte molecules is proposed. The method employs the energy transfer between two or more fluorescent chromophores in a carefully selected polymer matrix. In one preferred embodiment, signal amplification has been achieved in the fluorescent sensing of dimethyl methylphosphonate (DMMP) using two dyes, 3-aminofluoranthene (AM) and Nile Red (NR), in a hydrogen bond acidic polymer matrix. The selected polymer matrix quenches the fluorescence of both dyes and shifts dye emission and absorption spectra relative to more inert matrices. Upon DMMP sorption, the AM fluorescence shifts to the red at the same time the NR absorption shifts to the blue, resulting in better band overlap and increased energy transfer between chromophores. In another preferred embodiment, the sensitive material is incorporated into an optical fiber system enabling efficient excitation of the dye and collecting the fluorescent signal form the sensitive material on the remote end of the system. The proposed method can be applied to multichromophore luminescence sensor systems incorporating N-chromophores leading to N-fold signal amplification and improved selectivity. The method can be used in all applications where highly sensitive detection of basic gases, such as dimethyl methylphosphonate (DMMP), Sarin, Soman and other chemical warfare agents having basic properties, is required, including environmental monitoring, chemical industry and medicine.

8 Claims, 8 Drawing Sheets

Nile Red 3-aminofluoranten

BSP3

METHOD OF SIGNAL AMPLIFICATION IN MULTI-CHROMOPHORE LUMINESCENCE SENSORS

BACKGROUND OF THE INVENTION

1. Field of the Invention

The present invention relates to the methods for signal amplification in the detection of target molecules with luminescence-based sensors. The amplification involves energy transfer between two or more fluorescent chromophores in a carefully selected polymer matrix. The developed technology can be applied to any luminescence sensors comprising donor-acceptor pairs, and it can be generalized to multichromophore systems with n-chromophores leading to n-fold signal amplification and improved selectivity.

In one preferred embodiment, the signal amplification has been demonstrated experimentally in the fluorescent sensing of dimethyl methylphosphonate (DMMP) using two dyes, 3-aminofluoranthene (AM) and Nile Red (NR), in a hydrogen bond acidic polymer matrix. The selected polymer matrix quenches the fluorescence of both dyes and shifts dye emission and absorption spectra relative to more inert matrices. Upon DMMP sorption, the AM fluorescence shifts to the red. At the same time the NR absorption shifts to the blue, resulting in better band overlap and increased energy transfer between chromophores.

In another preferred embodiment, the sensitive material is incorporated into an optical fiber system enabling efficient excitation of the dye and collecting the fluorescent signal form the sensitive material on the remote end of the system.

The method can be used in all applications where highly sensitive detection of basic gases, such as dimethyl methylphosphonate (DMMP), Sarin, Soman and other chemical warfare agents having basic properties, is required, including environmental monitoring, chemical industry and medicine.

2. Information Disclosure Statement

Today, there is a high demand for chemical sensor for detecting low concentration levels of analytes present in the liquid and gaseous phase. Selectivity to target molecules is also highly desired. Traditional methods of quantitative detection of analytes based on gas chromatography and mass spectrometry require complex laboratory equipment. Among modern approaches for the real time monitoring of gaseous analytes, mainly three kinds of sensing elements have been investigated: microelectrodes, quartz crystal microbalance and surface acoustic wave devices. Generally all these methods are based on detection of only one parameter—signal intensity. Therefore reliable analyte identification requires significant increasing the number of individual sensors in the detector array.

Meanwhile, optical chemosensors, especially fluorescence-based chemosensors can provide many kinds of complex information, including changes in intensity, wavelengths and spectral shape, fluorescence lifetime. Hence such promising approach allowing detection of many parameters simultaneously should make possible fabrication of highly sensitive, robust, multi-analyte-detecting arrays with fewer independent sensors. Moreover, the possibility of remote sensing using optical fluorescence technique offers many serious advantages over other traditional methods of real-time monitoring of toxic gases and pollutants.

Most of the luminescence sensory materials known today consist of chromophores isolated in an inert matrix and cannot use the amplification effect resulting from energy migration/transfer in the excited states. Meanwhile the luminescence sensitivity can be considerably increased by the use of radiationless direct energy transfer (RDET) or emissive energy transfer (EET) between donor and acceptor chromophores isolated in an inert matrix. RDET is a distance-dependent transfer of electronic excitation from donor to acceptor due to dipole-dipole interaction and EET is a result of the acceptor reabsorption of the donor emission.

The present invention suggests new approach to the highly sensitive and selective detection of analyte employing the energy transfer between two or more fluorescent chromophores in a carefully selected polymer matrix. A quantitative model has been derived that can be applied to any luminescence sensors comprising donor-acceptor pairs, and it can be generalized to multichromophore systems with n-chromophores leading to n-fold signal amplification and enhanced sensor selectivity.

OBJECTS AND SUMMARY OF THE INVENTION

It is an object of the present invention to improve performance of chemical sensors of analyte molecules by employing the effect of the signal amplification due to energy transfer between two sensory chromophores isolated in special polymer matrix.

Another object of the invention is to provide a quantitative model that can be applied to any luminescence sensors comprising donor-acceptor pairs, and it can be generalized to multichromophore systems with n-chromophores leading to n-fold signal amplification.

A further object is to provide simple and efficient method of detection of the fluorescence signal by measuring enhancement of the fluorescence of acceptor chromophore at the excitation of donor chromophore in the presence of target molecules.

A further object is to provide a selection of efficient sensitive fluorescent material comprising a film of Nile Red (NR, acceptor chromophore) and 3-aminofluoranten (AM, donor chromophore) dyes having functional basic group and isolated in BSP3 polymer matrix that is a strong hydrogen bond acidic polymer.

Another object is to provide efficient method of processing the fluorescent signal from the sensitive material.

Still another object is to provide a possibility of remote monitoring of large contaminated area by incorporating the sensitive fluorescent material into an optical fiber system.

An additional object of the invention is to provide a method for fabrication of the fiber-optic fluorescence sensors achieving efficient excitation of the sensitive material and efficient collecting the fluorescence signal.

Briefly stated, the present invention provides a method of signal amplification in luminescence based chemical sensors where energy transfer effect between donor and acceptor chromophore can considerably increase the response signal with respect to mono chromophore sensor. This approach can be applied to any bi- or multichromophore sensors for detection of analyte molecules in gases or liquids. In particular, a signal amplification was demonstrated in the fluorescent sensing of dimethyl methylphosphonate (DMMP) using two dyes, AM and NR, in a hydrogen bond acidic polymer matrix. The selected polymer matrix quenches the fluorescence of both dyes and shifts dye emission and absorption spectra relative to more inert matrices. Upon DMMP sorption, the AM fluorescence shifts to the red. At the same time the NR absorption shifts to the blue, resulting in better band overlap and increased energy transfer between chromophores. Importantly that this also provides the better selectivity to DMMP vapors with respect to monochromophore sensor. The method can be used in fluorescence chemical sensors of basic gases for different applications including environmental monitoring, control of industrial processes and medicine.

The above, and other objects, features and advantages of the present invitation will become apparent from the following description read in conjunction with the accompanying drawings.

DESCRIPTION OF PREFERRED EMBODIMENTS

Figure 1:
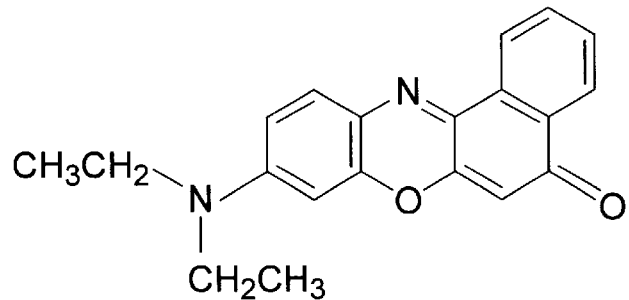
FIG. 1 shows the structure of Nile Red, 3-aminofluoranthene dyes and BSP3 polymer.
Figure 1:
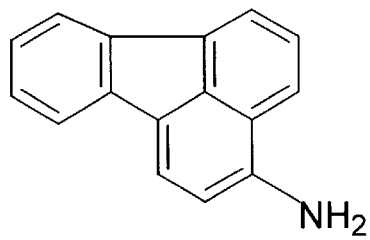
Figure 1:
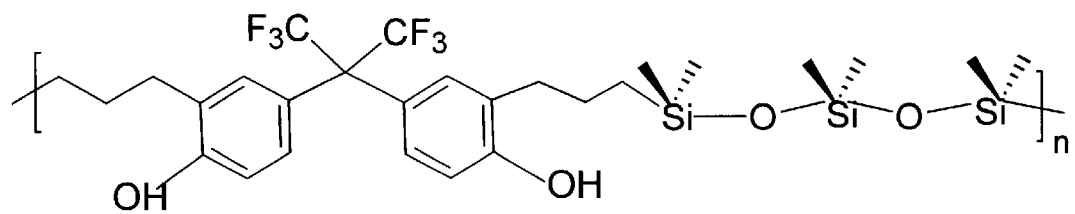

The invention provides a new method in the field of luminescence based sensors employing energy transfer effect between donor and acceptor chromophores that considerably increase the response signal with respect to a mono chromophore sensor. This approach can be applied to any bi- or multichromophore sensors for detection of analyte molecules in gases or liquids. The proposed general method can be used for the design of many different fluorescence-based sensory devices.

The proposed method of the signal amplification in the bi- and multichromophore sensors can be explained using the following quantitative model.

Let us consider the fluorescence enhancement as a mechanism of the signal transduction, however the same approach can be applied to the fluorescence quenching. Sensitivity and intensity of a sensor signal can be introduces as $S=I/I^0$ and $I$, respectively, where $I^0$ and $I$ are fluorescence intensities prior and after analyte exposure. Then for monochromophore system balance equations prior and after analyte exposure are given by, $$0 = -k^0 n^0 + JN^0$$

$$0 = -kn + JN \quad (1)$$

where, $n^0$, $k^0$ and $n$, $k$ are populations and deactivation rates (inverse lifetimes) of exited chromophores prior and after analyte exposure, N is the number of chromophores transferred to the new excited state after analyte exposure, $N^0$ is the total number of chromophores and J is the intensity of excited light. The general expression for signal intensity is:

$$I = \frac{k_r}{k_r + k_d} J \quad (2)$$

where $k_r$ and $k_d$ are radiation and radiationless deactivation rates, $k=k_r+k_d$. Usually, the radiationless processes ($k_d$ parameter) is more sensitive to change of the chromophore environment. Therefore in the following we will consider only $k_d$ changes keeping $k_r$ as a constant. Then the monochromophore sensor sensitivity, $S_M$, is given by, $$S_M = \frac{I}{I^0} = \frac{k_0 N}{k N^0} = K_B \times \frac{k_0}{k} \quad (3)$$

here $K_B = N/N^0$ is the binding constant for analyte-chromophore interaction. We omit the remaining part of the chromophore molecules ($N^0-N$) at unchanged state under analyte exposure due to condition $k^0 \gg k$ (strong fluorescence enhancement). If initially there is no fluorescence at all ($I^0=0$), then sensitivity S can be defined as $S_M=I$.

The bi-chromophore scheme proposes to selectively excite only donor chromophores and detect the response fluorescence signal from acceptor chromophores. Acceptor fluorescence in this case is a result of the direct energy transfer in accordance with RDET (Förster mechanism), or EET (reabsorbtion). We begin consideration with RDET and then demonstrate that substitution to the reabsorption does not change the final formula. Prior analyte exposure, the balance equations for donor and acceptor populations are given by, $$0 = -(k_D^0 + k_{TR}^0) n_D^0 + JN_D^0 \quad (4)$$
$$0 = -k_A^0 n_A^0 + k_{TR}^0 n_D^0 N_A^0$$

and $$I_A^0 = \frac{k_A^{0r} k_{TR}^0}{k_A^0 (k_{TR}^0 + k_D^0)} J N_A^0 N_D^0 \quad (5)$$

where $k^0_D$, $k^0_A$, are donor and acceptor deactivation rates and $k^0_{TR}$ is the RDET rate between them; $k^{0r}_A$ is the radiation deactivation rate of the acceptor, $N^0_D$ and $N^0_A$ is the total number of donor and acceptor chromophores. In the most general case the analyte exposure can affect both the donor and acceptor deactivation rates and also the energy transfer between them. Then, the fluorescence intensity after exposure can be presented in the same way as Eq.(5), $$I_A = \frac{k_A^{0r} k_{TR}}{k_A(k_{TR} + k_D)} J N_A N_D \qquad (6)$$

where $N_A = K_{BA} N_A^0$ and $N_D = K_{BD} N_D^0$ are number of acceptor and donor chromophores transferred to the new excited state and other parameters have the same meaning as in Eq.(5) (the parameters without index 0 correspond to their values changed after exposure). The relation $k_{TR} < k_D$ is a reasonable condition since the usual concentration of chromophores in a solid matrix can not provide an average distance between donor and acceptor less than typical Förster radius, which is 20–60 Å for most organic compounds. Finally, we can get the sensitivity $S_B$ of the bi-chromophore sensor, $$S_B = \frac{I_A}{I_A^0} = K_{BD} \times K_{BA} \times \frac{k_D^0}{k_D} \times \frac{k_A^0}{k_A} \times \frac{k_{TR}}{k_{TR}^0} \qquad (7)$$

Comparison of Eq.(7) with Eq.(3) demonstrates the sensitivity amplification for bi-chromophore system with respect to mono-chromophore one. For example, let us assume that for strong analyte-chromophore binding ($K_{BA} = K_{BD} \geq 1$) analyte exposure induces fluorescence enhancement of the donor and acceptor fluorescence intensity and RDET between them in two times ($k_D^0 = 2k_D$, $k_A^0 = 2k_A$, $k_{TR}^0 = k_{TR}/2$). Then the bi-chromophore sensitivity will be in four times higher than the sensitivity of mono-chromophore system ($S_B = 4S_M$).

If reabsorption of the donor emission by acceptor chromophores (EET) is the main mechanism of energy transfer, then Eqs.(4) and (5) should be modified as follows:

$$0 = -k_D^0 n_D^0 + J N_D^0 \qquad (8)$$
$$0 = -k_A^0 n_A^0 + J_{RB}^0 N_A^0$$

and $$I_A^0 = \frac{k_A^{0r}}{k_A^0} J_{RB}^0 N_A^0 N_D^0 \qquad (9)$$

The reabsorption intensity is $J_{RB}^0 \sim I_{OV}^0 \times Q_D^0$, where $I_{OV}^0$ is the integral characterizing overlapping between acceptor absorption and donor fluorescence spectra and $Q_D^0$ is the donor quantum yield. Following the above procedure for Eq.(7) we can derive the expression for bi-chromophore sensitivity $S_B$ in the reabsorption case, $$S_B = \frac{I_A}{I_A^0} = K_{BD} \times K_{BA} \times \frac{k_D^0}{k_D} \times \frac{k_A^0}{k_A} \times \frac{I_{OV}}{I_{OV}^0} \qquad (10)$$

Eq.(10) is similar to Eq.(7), where RDET rate ($k_{TR}$) is substituted by the overlapping integral ($I_{OV}$). The stronger is overlapping between donor and acceptor spectra the higher are $I_{OV}$ and $k_{TR}$ values. However, there is a difference between Eqs.(10) and (7). In accordance with Förster model $k_{TR} \sim (R_F)^3$ and Förster radius $R_F \sim I_{OV} \times Q_D \sim I_{OV}/k_D$. After substitution of $k_{TR}$ in Eq.(7) we found that RDET sensitivity will non-linear depend on parameters $k_D^0/k_D$ and $I_{OV}/I_{OV}^0$. Thus, despite the different nature of the energy transfer between donor to acceptor chromophores both RDET and EET provide amplification of the sensitivity for bi-chromophore sensory films.

Bi-chromophore sensor can be generalized to n-chromophore sensor as follows:

$$S_n = K_{Bn} \times \frac{k_n^0}{k_n} \prod_{i=1}^{n-1} K_{Bi} \times \frac{k_i^0}{k_i} \times \frac{S_i}{S_i^0} \qquad (11)$$

where $K_{Bi}$ is the binding constant of analyte to i chromophore; $k_i^0$ and $k_i$ are deactivation constants of i chromophore prior and after analyte exposure, and $S_i^0$ and $S_i$ are RDET rate or overlapping integral between i and i+1 chromophores prior and after analyte exposure. In such sensing scheme only the first chromophore should be excited (energy donor, i=1) and then its excited energy is transferred consequently through other ones to the final acceptor chromophore (i=n) that emits the fluorescence. If the binding constants are rather high ($K_{Bi} \leq 1$), and chromophore-analyte interaction leads to fluorescence enhancement ($k_i^0/k_i > 1$) then the n-fold amplification of the sensitivity occurs with respect to mono-chromophore sensors. The amplification can be even more if analyte binding induces the increase of the energy transfer between chromophores ($S_i/S_i^0 > 1$).

In the preferred embodiment shown in FIG. 1 a solvatochromic dyes Nile Red (NR, energy acceptor) and 3 aminofluoranten (AM, energy donor) are employed as active emissive elements of the bi-chromophore sensors. Two polymers BSP3 (FIG. 1) and PMMA were tested as a matrix for these dyes. BSP3 has strong hydrogen-bond acidic properties. PMMA that does not have hydrogen-bond groups was used as a reference.

Figure 2:
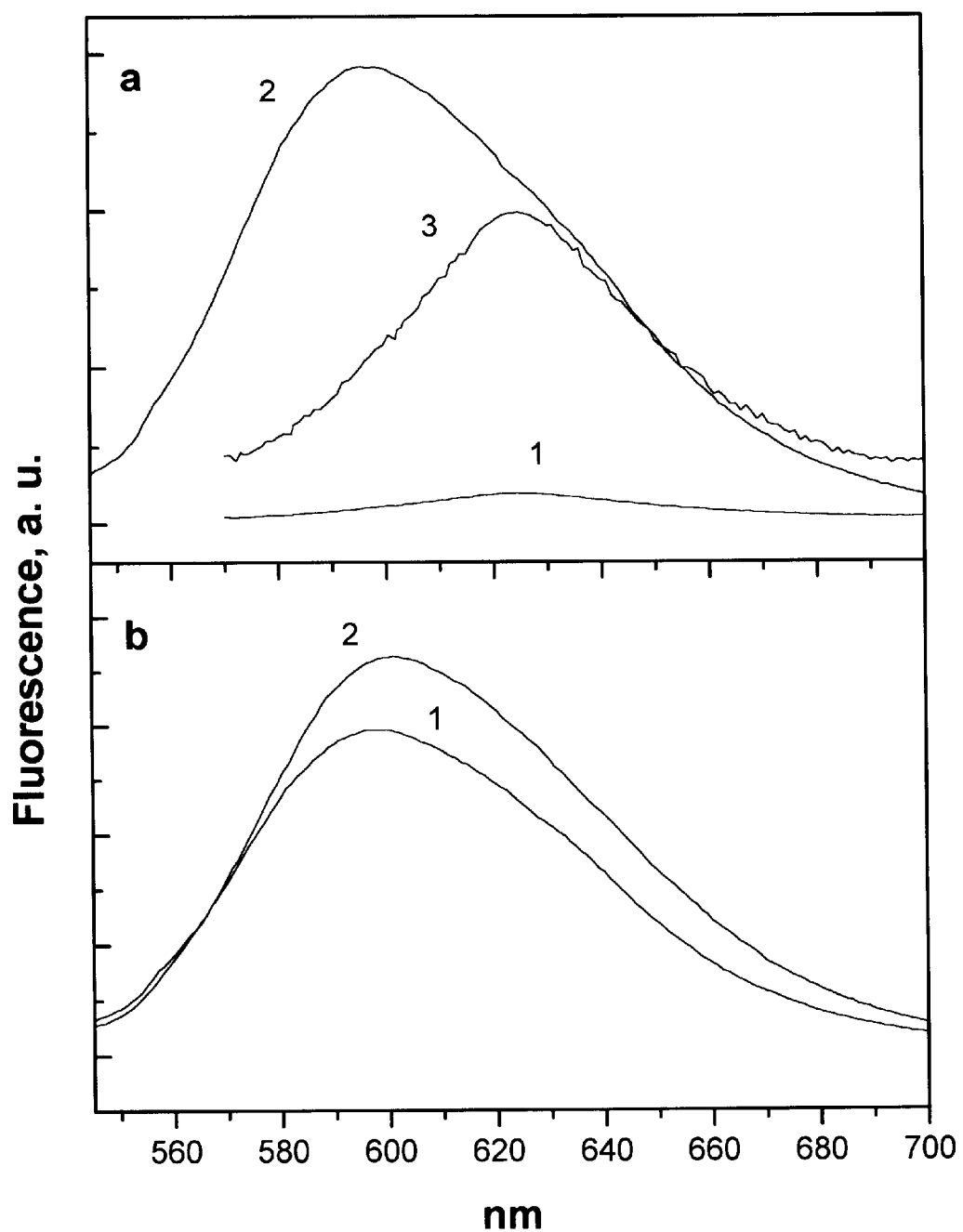
FIG. 2 shows Nile Red fluorescence spectra before (1) and after (2) DMMP exposure in BSP3 (a) and PMMA (b) spin cast films ($\lambda_{ex}$=530 nm). Spectrum (3) is spectrum (1)×10.

FIG. 2 demonstrates the pronounced NR fluorescence enhancement and the spectral blue shift under exposure to dimethyl methylphosphonate (DMMP) saturated vapors for BSP3 matrix and rather small changes without spectral shift for PMMA matrix. DMMP is a strong basic vapor usually employed as a simulant of chemical warfare agents (CWA), such as Sarin, Soman and other basic CWA agents. The mechanism of DMMM sorption in the NR/BSP3 sensory films was described in detailed in our patent application Ser. No. 101565535.

Figure 3:
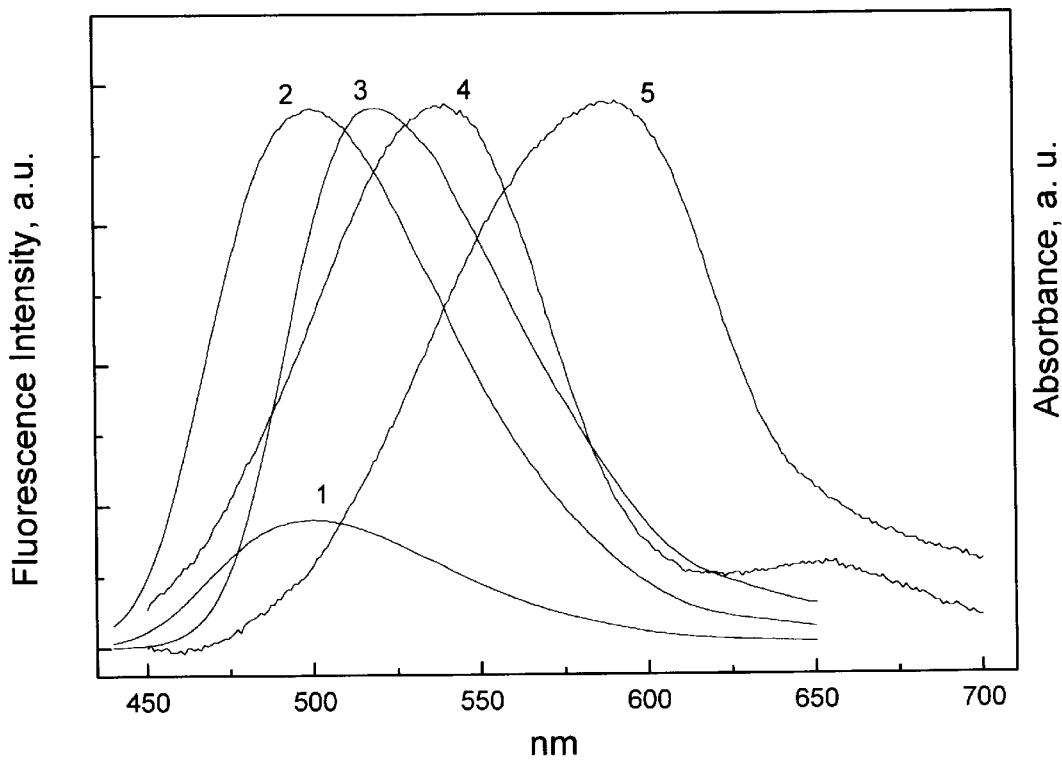
FIG. 3 demonstrates spectral shifts of AM fluorescence and NR absorbance in BSP3 films upon DMMP exposure. AM fluorescence spectra in AM/BSP3 films before (1) and after (3) DMMP exposure show the fluorescent enhancement and red shift. Spectrum 2 is spectrum 1 normalized to spectrum 3. NR absorbance in NR/BSP3 films before (5) and after (4) DMMP exposure normalized to spectrum 3, showing the blue shift in absorbance.
Figure 4:
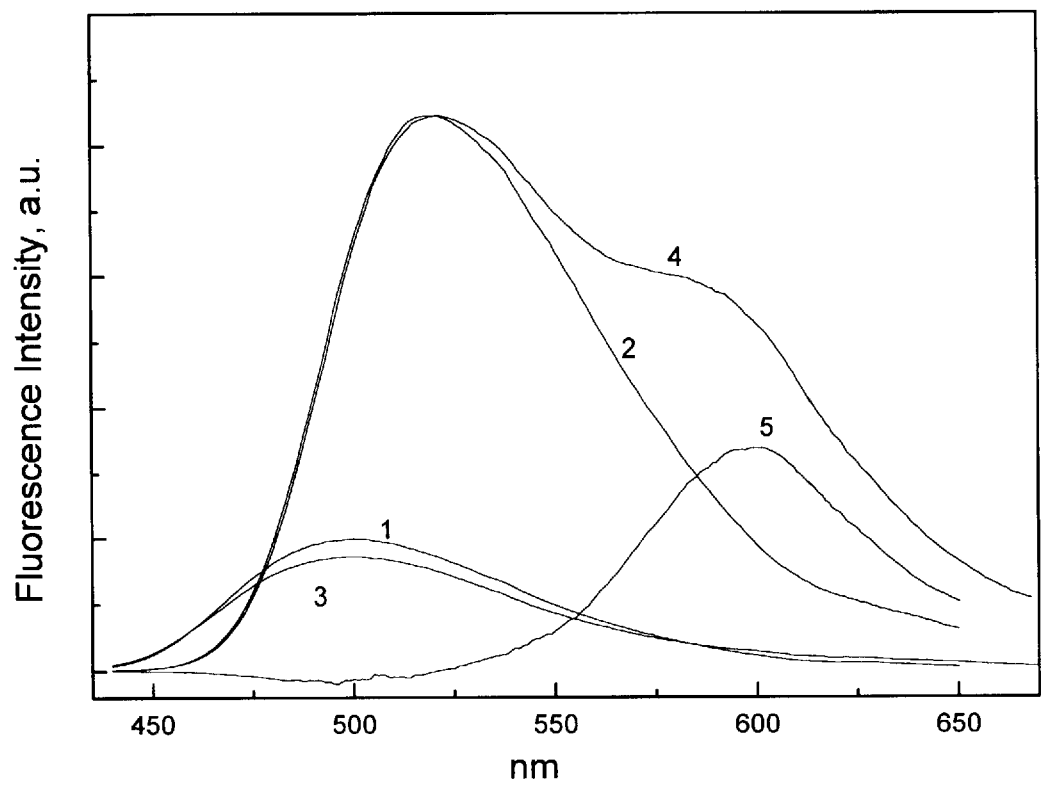
FIG. 4 demonstrates fluorescence of AM-NR/BSP3 films before (3) and after (4) DMMP exposure ($\lambda_{ex}$=400 nm). For comparison, it also shows the fluorescence ($\lambda_{ex}$=400 nm) of AM/BSP3 before (1) and after (2) DMMP exposure, where 2 has been normalized to the height of 4 (spectrum 1 was multiply by the same factor that spectrum 2). Then the difference between 4 and 2 gives 5, the fluorescent peak from NR in the AM-NR/BSP3 film which is in agreement with results from NR/BSP3 films under DMMP exposure as shown in FIG. 2.

Fluorescence of AM isolated in BSP3 films under DMMP exposure also shows an enhancement however in contrast to NR it exhibits a red spectral shift (FIG. 3). NR absorption in BSP3 films is blue shifted under exposure to DMMP saturated vapors. As a result, there is strong overlap of the AM fluorescent band and the NR absorption band. Thus the analyte exposure induces an increase of the energy transfer between AM (donor) and NR (acceptor) and fluorescence enhancement for both chromophores. Such situation is an ideal for demonstration of the amplification effect in the bi-chromophore system according to the proposed model (Eqs.(7), (8)). As result, strong NR fluorescence was observed in bi-chromophore AM-NR/BSP3 sensory films exposed to DMMP vapors. FIG. 4 shows the fluorescence spectra of AM-NR/BSP3 films before and after DMMP exposure (spectra 3 and 4, respectively). The samples were excited at $\lambda_{ex}$=400 nm in the absorption band of AM, where NR practically does not absorb light. Therefore, prior DMMP exposure only AM fluorescence band has been observed without any sign of NR fluorescence (the condition of selective donor excitation is fulfilled here). DMMP exposure leads to appearance of the intensive NR fluorescence band (590 nm) comparable with the AM emission (spectrum 3) as result of signal amplification (strong spectral overlapping and fluorescence enhancement of both chromophores).

Figure 5:
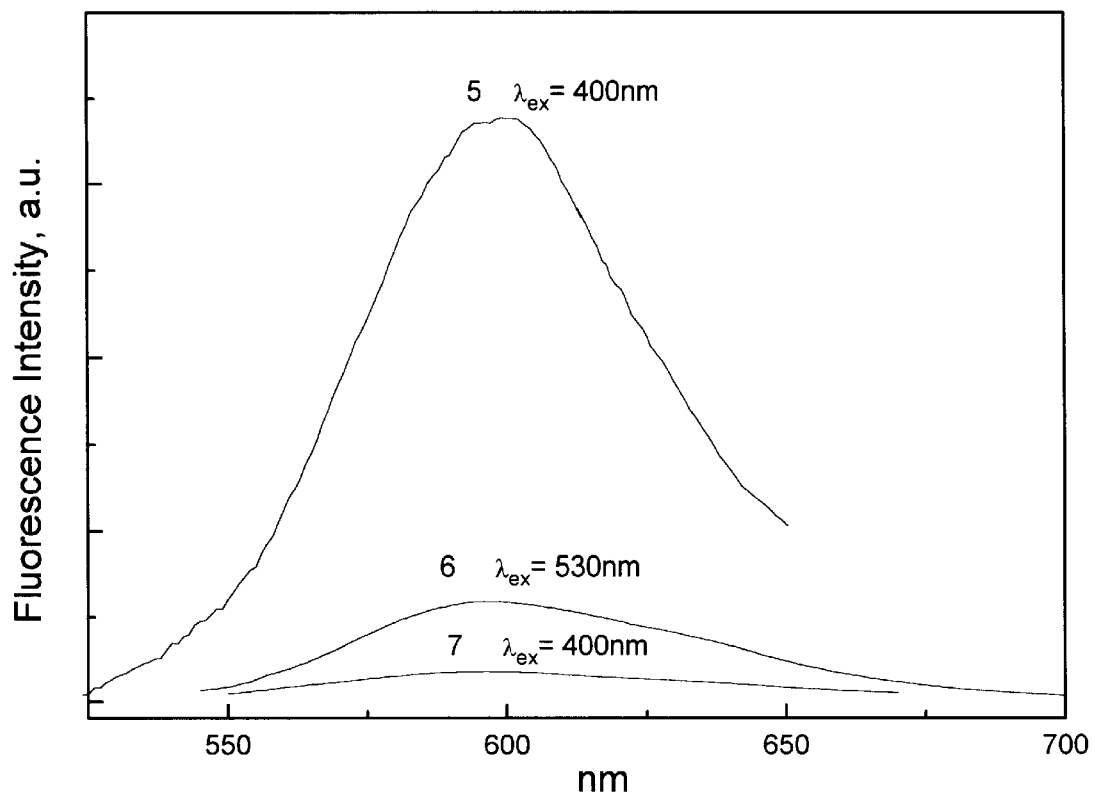
FIG. 5 shows the fluorescence spectra of AN-NR/BSP3 films (5) and NR/BSP3 films (6,7) after DMMP exposure. Spectrum 5 is the same one as in the FIG. 4.

In an additional preferred embodiment, the processing of obtained spectra and comparison with mono-chromophore sensor has been made. In order to estimate the bi-chromophore sensitivity ($S_B$ value) we should extract NR fluorescence band from the composed spectrum of NR/AM emission (spectrum 4 in FIG. 4) and take the ratio of its intensity to that of NR emission before exposure. The fluorescence spectrum of AM/BSP3 film after DMMP exposure was used as a reference (spectrum 2 in FIG. 4). Finally, the spectrum 5 is a result of subtraction of the spectrum 2 from spectrum 4 (FIGS. 4, 5). The same procedure was applied to extract the NR fluorescence band before exposure in the AM-NR/BSP3 films (FIG. 5, spectrum 7). The ratio of peak intensity of spectrum 5 ($I_A$ value, after exposure) to that of spectrum 7 ($I^0_A$ value, prior exposure) gives $S_B$~250, which is considerably higher than $S_M$=15 (mono-chromophore sensitivity) obtained for NR/BSP3 film at $\lambda_{ex}$=400 nm and $\lambda_{ex}$=530 nm (FIG. 2a). Also, an absolute magnitude of the response signal for AM-NR/BSP3 films (FIG. 5) after DMMP exposure exceeds in more than one order of magnitude that for NR/BSP3 film at the same excitation wavelength ($\lambda_{ex}$=400 nm) and more than 5 times for $\lambda_{ex}$=530 nm. This is another advantage of the bi-chromophore sensing with respect to the mono-chromophore detection scheme.

Figure 6:
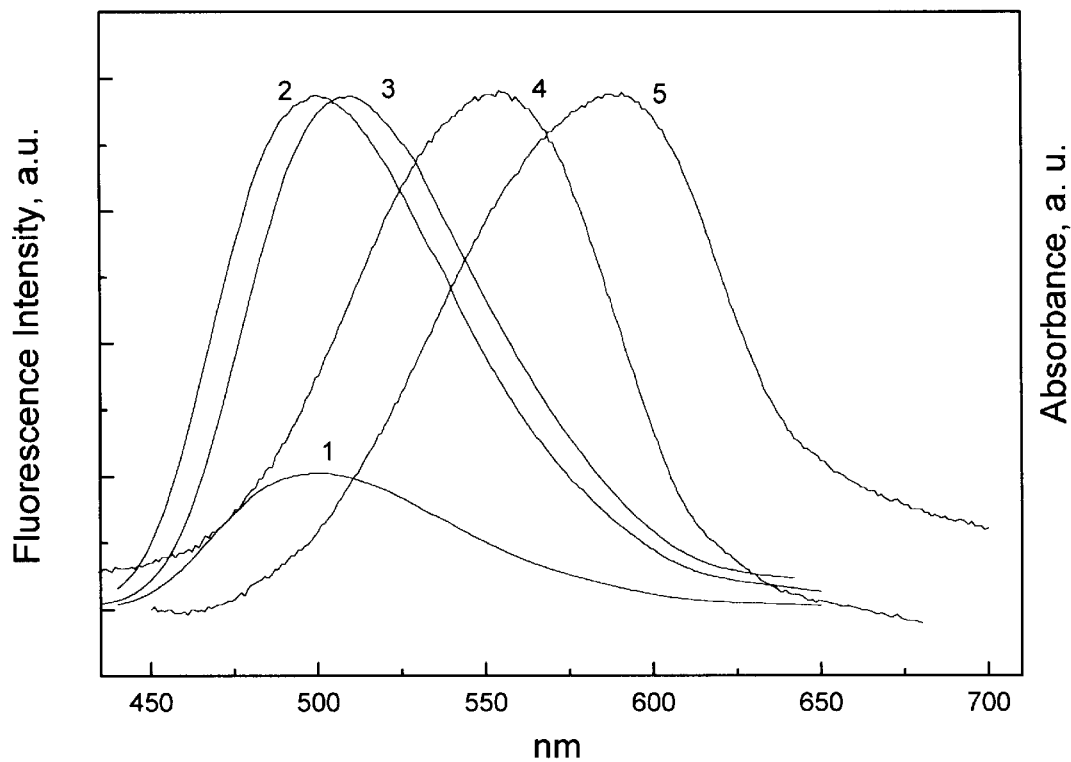
FIG. 6 shows normalized NR absorption (4,5) and AM fluorescence (2,3) spectra in spin cast NR/BSP3 and AM/BSP3 films prior (2,5) and after (3,4) ethanol exposure. Spectrum (2) is the normalized spectrum (1) that demonstrate the AM fluorescence enhancement.
Figure 7:
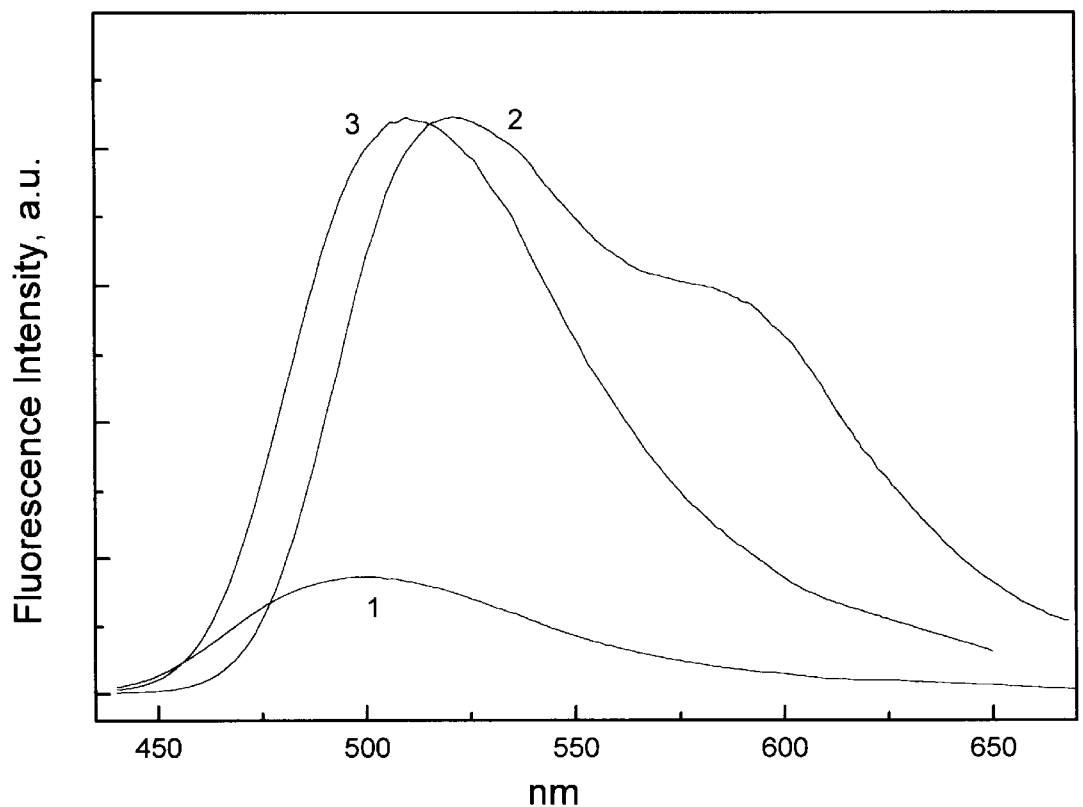
FIG. 7 shows the fluorescence spectra of AM-NR/BSP3 films prior (1) and after DMMP (2) and ethanol (3) exposure. Spectrum (3) is normalized on the maximum of spectrum (2).

In another preferred embodiment we take advantage of demonstrated improved selectivity of the bi-chromophore AM-NR/BSP3 films. Strong overlapping between donor and acceptor spectra under exposure of the specific analyte is a rather unique property of the proposed film composition. It means that such system should be very selective to given analyte diminishing the false response from other interfering vapors. If overlapping between donor emission and acceptor absorption cannot provide an efficient energy transfer, the response signal will be dramatically low. The experimental results presented in FIGS. 6 and 7 confirm this idea. We chose saturated vapor of ethanol as an interfering gas, which can induce the false response in the mono-chromophore NR/BSP3 film. As one can see form FIG. 7, the ethanol exposure does not result in any NR fluorescence in AM-NR/BSP3 films. This is consistent with less spectral overlapping under ethanol exposure (FIG. 6) as compared with that in the case of DMMP exposure (FIG. 3). Hence, the AM-NR/BSP3 bi-chromophore films are completely insensitive to the interfering ethanol vapors as distinct from the mono-chromophore NR/BSP3 films. Note that the concentration of the ethanol saturated vapor in ~25 times exceeded concentration of DMMM saturated vapor. Also we tested other organic vapors such as benzene and chloroform and did not find any sizable NR fluorescence.

In another preferred embodiment the proposed method of detection of molecules of analyte molecules employs sensitive NR-AM/BSP3 compound incorporated into a waveguide or into a fiber-optic system having a flexible fiber-optic probe exhibiting enhanced sensitivity and improved reliability, yet low in cost. In one configuration, the fluorescent sensitive material is excited with a compact blue laser diode or LED generating, for example, at wavelength 405–430 nm.

In still another embodiment the light delivery and collection is performed using a U-bent fiber. It is known that due to sharp bending of the multimode fiber with radius of bending of about 1–2 mm the light escapes from the fiber core into its low-index cladding. After Fresnel reflection at the interface between the cladding and an external low-index media (or air), almost 80% of the light returns back into the fiber core. If the bent region of the fiber is coated with a sensitive fluorescent film, then the returned light will contain also some part of the fluorescent signal. In spite of very simple and cost-efficient design of such a fiber probe it does not provide maximum sensitivity. Length of the bent fiber region is relatively small resulting in a weak fluorescence response signal. Such fiber probe can be used in the applications that do not require very high sensitivity. In order to enhance the sensitivity one should increase the distance of light propagation in the fluorescence film. This is achieved, for example, by removing fiber cladding in the U-bent region (polishing it down to the fiber core) and depositing the fluorescent sensitive material directly on the fiber core.

Figure 8:
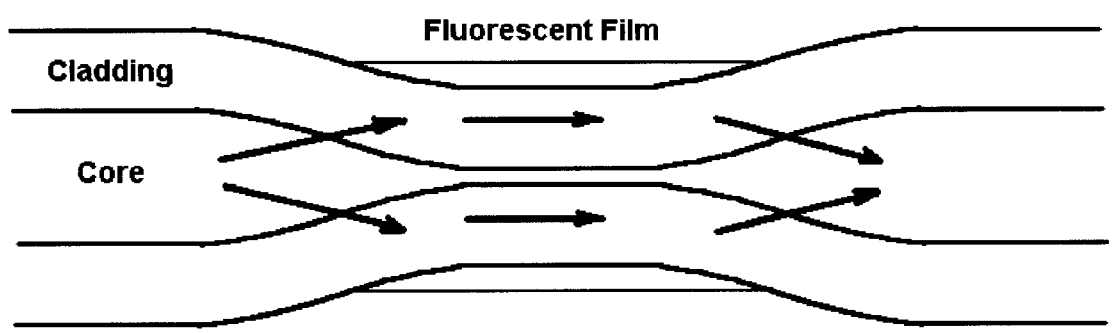
FIG. 8 Shows double tapered fiber probe.

In another preferred embodiment shown in FIG. 8 the light propagation distance of the fluorescent material is increased by employing a double tapered fiber configuration. It is known that as the fiber diameter decreases the light escapes from the fiber core and propagates in its cladding. The cladding coated with or made from thin fluorescent film guides the light due to total internal reflection at the cladding-air interface. At the second taper, where the fiber diameter increases, the light containing also the fluorescence signal re-couples back into the fiber core. Magnitude of the fluorescence signal extracted form the sensitive film by evanescent modes is proportional to the distance of light propagation through the polymer film. In the case of a double taper configuration the distance can be made as large as ten centimeters providing very high sensitivity. Removing of the fiber cladding and depositing the sensitive fluorescent material directly onto the fiber core allows further increasing the system sensitivity.

In additional preferred embodiment the sensitive fluorescent material is directly incorporated into the fiber-optic system playing a role of an optical waveguide. In that case the system sensitivity is enhanced by forcing the light to propagate through the sensitive material.

Thus, this method provides an efficient fluorescence-based means for highly sensitive and selective detection of the analyte molecules. As a general technology, the proposed method can find many useful applications for detecting different toxic gases and pollutants in water, including dimethyl methylphosphonate (DMMP) and such important chemical warfare agents as Sarin and Soman, as required for environmental monitoring, chemical industry and medicine.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

This invention was made with Government support under Grant DE-FG02-99ER82737 awarded by the Department of Energy. The Government has certain rights in this invention.

What is claimed is:

1. A method of detecting molecules of basic gases and other analyte molecules in gaseous or liquid media, employing a sensitive material having at least two fluorescent components incorporated into a polymer matrix, comprising the steps of:

exciting at least one of said fluorescent components (energy donor) with at least one light source generating at the wavelengths required for efficiently stimulating the fluorescence of said donor fluorescent component, collecting the fluorescent light signal from the other of said fluorescent components (energy acceptor) with a light collecting system, and detecting and processing the fluorescent light signal from said sensitive material at the wavelength corresponding to maximum of the fluorescent signal, wherein said donor fluorescent component, which is Nile Red (NR), is chosen to provide the efficient energy transfer to said acceptor fluorescent component, which is 3-aminofluoranthene (AM), leading to amplification of the response signal, and both said fluorescent components are isolated in a strong hydrogen bond acidic polymer, which is BSP3, that is synthesized for sorption of basic gases, such as dimethyl methylphosphonate (DMMP), Sarin, Soman and other chemical warfare agents having basic properties.

2. A method of molecules of basic gases of claim 1, wherein said sensitive material has N>2 fluorescent components leading to N-fold signal amplification and providing improved selectivity to basic vapor.

3. A method of detecting molecules of basic gases of claim 1, wherein said fluorescent sensitive material is incorporated into a waveguiding system delivering light from said at least one light source and effectively collecting the signal light from said fluorescent sensitive material.

4. A method of detecting molecules of basic gases of claim 3 wherein at least one section of said waveguiding system is made from said fluorescent sensitive material operating as a waveguide at wavelengths of said excitation light and said fluorescent signal light.

5. A method of detecting molecules of basic gases of claim 3 wherein said waveguiding system incorporates at least one optical fiber having at least one sharp U-bend and said fluorescent sensitive material having refractive index not less than the refractive index of the medium in which molecules of the basis gas under detection are present is deposited on outer surface of the fiber in the region of its said U-bend.

6. A method of detecting molecules of basic gases of claim 5, wherein cladding of said fiber in said outer region of U-bend is removed before depositing said fluorescent sensitive material improving excitation of the fluorescent sensitive materials and collecting the fluorescent signal light.

7. A method of detecting molecules of basic gases of claim 3, wherein said waveguiding system incorporates at least one optical fiber having at least one section with double tapered geometry characterized by decreasing and then increasing fiber diameter, said fluorescent sensitive material having refractive index not less than the refractive index of the medium in which molecules of the basis gas under detection are present is deposited on the surface of said fiber in its said double tapered region.

8. A method of detecting molecules of basic gases of claim 7, wherein cladding of said fiber in said double tapered region is removed before depositing said fluorescent sensitive material improving excitation of the fluorescent sensitive materials and collecting the fluorescent signal light.

* * * * *